US008969390B2

(12) United States Patent
Klug et al.

(10) Patent No.: US 8,969,390 B2
(45) Date of Patent: *Mar. 3, 2015

(54) COMPOSITION CONTAINING SORBITAN MONOCAPRYLATE AND ANTIMICROBIAL SUBSTANCES

(75) Inventors: Peter Klug, Grossostheim (DE); Sonja Gehm, Bad Soden am Taunus (DE); Guiseppina Kluth, Kelkheim (DE); Franz-Xaver Scherl, Burgkirchen (DE); Maurice Frederic Pilz, Frankfurt am Main (DE)

(73) Assignee: Clariant Finance (BVI) Limited, Tortola (VG)

( * ) Notice: Subject to any disclaimer, the term of this patent is extended or adjusted under 35 U.S.C. 154(b) by 0 days.

This patent is subject to a terminal disclaimer.

(21) Appl. No.: 13/321,178

(22) PCT Filed: May 11, 2010

(86) PCT No.: PCT/EP2010/002919
§ 371 (c)(1),
(2), (4) Date: Jan. 3, 2012

(87) PCT Pub. No.: WO2010/136121
PCT Pub. Date: Dec. 2, 2010

(65) Prior Publication Data
US 2012/0101135 A1 Apr. 26, 2012

(30) Foreign Application Priority Data
May 23, 2009 (DE) .................. 10 2009 022 444

(51) Int. Cl.
*A01N 43/08* (2006.01)
*A61Q 19/00* (2006.01)
*A01N 43/80* (2006.01)
*A61K 31/34* (2006.01)
*A61K 31/35* (2006.01)
*A61Q 5/00* (2006.01)
*A01N 37/06* (2006.01)
*A01N 37/10* (2006.01)
*A01N 43/16* (2006.01)
*A61K 8/49* (2006.01)
*A61Q 1/04* (2006.01)
*A61Q 1/14* (2006.01)
*A61Q 5/02* (2006.01)
*A61Q 5/06* (2006.01)
*A61Q 5/12* (2006.01)
*A61Q 15/00* (2006.01)
*A61Q 19/08* (2006.01)
*A61Q 19/10* (2006.01)

(52) U.S. Cl.
CPC .............. *A01N 37/06* (2013.01); *A01N 37/10* (2013.01); *A01N 43/08* (2013.01); *A01N 43/16* (2013.01); *A01N 43/80* (2013.01); *A61K 8/4973* (2013.01); *A61Q 19/00* (2013.01); *A61K 2800/524* (2013.01); *A61Q 1/04* (2013.01); *A61Q 1/14* (2013.01); *A61Q 5/02* (2013.01); *A61Q 5/06* (2013.01); *A61Q 5/12* (2013.01); *A61Q 15/00* (2013.01); *A61Q 19/002* (2013.01); *A61Q 19/08* (2013.01); *A61Q 19/10* (2013.01)
USPC ........... 514/345; 514/159; 514/372; 514/460; 514/461; 424/70.1

(58) Field of Classification Search
USPC .................... 514/345, 372, 460, 462; 424/59
See application file for complete search history.

(56) References Cited

U.S. PATENT DOCUMENTS

| 3,331,742 A | 7/1967 | Babayan |
| 4,637,930 A | 1/1987 | Konno et al. |
| 4,847,088 A | 7/1989 | Blank |
| 6,413,529 B1 | 7/2002 | Beerse et al. |
| 2003/0203070 A1* | 10/2003 | Lin et al. .................. 426/25 |
| 2005/0222276 A1 | 10/2005 | Schmaus et al. |
| 2007/0178144 A1 | 8/2007 | Hamayer et al. |
| 2008/0142023 A1 | 6/2008 | Schmid |
| 2008/0312195 A1 | 12/2008 | Simsch et al. |
| 2012/0015893 A1 | 1/2012 | Herrwerth et al. |
| 2012/0100085 A1 | 4/2012 | Klug et al. |

FOREIGN PATENT DOCUMENTS

| CA | 1231046 | 1/1988 |
| DE | 3328372 | 3/1984 |
| EP | 1813251 | 8/2007 |
| EP | 1972330 A2 * | 9/2008 |
| JP | H01313408 | 12/1989 |
| JP | H03168075 | 7/1991 |
| JP | H09291016 | 11/1997 |
| JP | 2002541181 | 12/2002 |
| JP | 2003238396 | 8/2003 |
| JP | 2007203288 | 8/2007 |
| WO | WO 2010108738 | 9/2010 |

OTHER PUBLICATIONS

International Search Report for PCT/EP2010/002919 mail date Nov. 15, 2011.
International Preliminary Report on Patentability for PCT/EP2010/002919, dated Feb. 28, 2012.

(Continued)

*Primary Examiner* — Ernst V Arnold
*Assistant Examiner* — Kyung Sook Chang
(74) *Attorney, Agent, or Firm* — Tod A. Waldrop

(57) ABSTRACT

The invention relates to liquid compositions which contain a) from 40 to 99.9% by weight of sorbitan monocaprylate and b) from 0.1 to 60% by weight of one or more antimicrobial substances selected from the group consisting of the components b1) to b5): b1) specific organic acids and the salts thereof, b2) specific formaldehyde donors, b3) specific isothiazolinones, b4) specific paraben esters and the salts thereof, and b5) specific pyridones and the salts thereof. The liquid compositions are suitable for the production of cosmetic, dermatological or pharmaceutical products.

10 Claims, No Drawings

(56) References Cited

OTHER PUBLICATIONS

International Search Report for PCT/EP2010/002918 mail date Jun. 30, 2011.
Database CA (Online), Chemical Abstracts Service, Columbus, Ohio (Sep. 29, 2000), Fukushima Noriko; "Water-soluble rinses for dishwashers", XP002643077.
Database CA (Online), Chemical Abstracts Service, Columbus, Ohio (Aug. 14, 2008), Mori Toshiki; "Transparent cleaners comprising nonionic surfactants", XP002643078.
Database CA (Online), Chemical Abstracts Service, Columbus, Ohio (May 12, 1984), Miura Takeshi, Ishida Katsuo; "Rinsing assistants", XP002643079. English abstract of JP 51056809.
Database CA (Online), Chemical Abstracts Service, Columbus, Ohio (May 12, 1984), Miura Takeshi, Ishida Katsuo; "Rinsing assistants", XP002643080. English abstract of JP 51068608.
Database CA (Online), Chemical Abstracts Service, Columbus, Ohio (Sep. 18, 2003), Miura Takeshi, et al.; "Coenzyme Q10-containing emulsions, and manufacture thereof", XP002643081. English abstract of JP 2003238396.
Database GNPD (Online), (Feb. 1999), Mintel; "Verzorgende Shampoo-Lang Harr", XP002662186.
English Abstract for JPH03168075, Jul. 19, 1991.
English Abstract for JPH09291016, Nov. 11, 1997.

* cited by examiner

COMPOSITION CONTAINING SORBITAN MONOCAPRYLATE AND ANTIMICROBIAL SUBSTANCES

The present invention relates to liquid compositions containing sorbitan monocaprylate and antimicrobial active ingredients.

Cosmetic, dermatological or pharmaceutical formulations and products in general offer, on the basis of the high water content, a favorable pH of between pH 5-8 and a promoting storage temperature of approximately 25° C., an ideal environment for the growth of microorganisms. Some ingredients used such as proteins or plant extracts can additionally serve as a source of nutrition for bacteria and fungi. Furthermore, microorganisms or their spores can reach the formulation or the product by means of ingredients contaminated therewith. As a cosmetic, dermatological or pharmaceutical formulation must be harmless for the user and, for example, skin irritation to serious infections of the eye can be induced by a microbial contamination of such a product, a cosmetic, dermatological or pharmaceutical formulation should be adequately protected against microbial attack.

This is in general achieved by the addition of antimicrobially active substances, "preservatives", to the formulation.

The antimicrobial active ingredient(s) employed should be metered here such that the growth of microorganisms in the formulation or the product is prevented, not only during storage, but also a bacterial count increase as a result of a new contamination on the part of the user is effectively suppressed by appropriate use.

The antimicrobial active ingredients should in this case destroy bacteria. and fungi as efficiently as possible, but at the same time be mild and harmless for human beings. In order to guarantee the latter, maximum use concentrations and application use such as application areas of the antimicrobial active ingredients, supported in scientific investigations, are legally controlled. In Europe, ANNEX VI of the Cosmetics Act applies in this case.

New knowledge on the toxicological potential of an antimicrobial active ingredient leads to a new evaluation on the part of the legislator. In recent years, the number of use intensifications of antimicrobial active ingredients has increased here.

In order to furthermore protect the consumer against the dangers triggerable by microbial attack, but also against the side-effects of antimicrobial active ingredients, it is advantageous to use as small amounts of antimicrobial active ingredients as possible. Mild and harmless effect enhancers of antimicrobial active ingredients offer the possibility of lowering the use concentration of the antimicrobial active ingredient even further without increasing the danger of the side-effects for human beings.

In order to keep the total amount of antimicrobial active ingredients in the cosmetic, dermatological or pharmaceutical formulation low, the object consisted in finding a dermatologically and toxicologically harmless substance that supports the antimicrobial action of antimicrobial active ingredients.

Surprisingly, it has now been found that the sorbitan monocaprylate already known and used in cosmetics as a surfactant and emulsifying agent fulfills exactly these conditions.

The subject of the present invention are therefore liquid compositions containing a) from 40 to 99.9% by weight, preferably from 45 to 99.5% by weight, particularly preferably from 50 to 99% by weight and especially preferably from 55 to 98% by weight, of sorbitan monocaprylate and b) from 0.1 to 60% by weight, preferably from 0.5 to 55% by weight, particularly preferably from 1 to 50% by weight and especially preferably from 2 to 45% by weight, of one or more antimicrobial active ingredients selected from the group consisting of the components b1) to b5)

b1) organic acids and their salts selected from benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts, b2) formaldehyde donors selected from DMDM hydantoin, imidazolidinyl urea, diazolidinyl urea and sodium hydroxymethylglycinate, b3) isothiazolinones selected from aqueous compositions containing from 20 to 80% by weight, preferably from 30 to 70% by weight and particularly preferably from 40 to 60% by weight, of methylisothiazolinone, chloromethylisothiazolinone, a mixture of methylisothiazolinone and chloromethylisothiazolinone in the ratio 1:3 and/or benzylisothiazolinone, b4) paraben esters and their salts selected from methylparaben, sodium methylparaben, ethylparaben, sodium ethylparaben, propylparaben, sodium propylparaben, isobutylparaben, sodium isobutylparaben, butylparaben and sodium butylparaben, b5) pyridones and their salts selected from 1-hydroxy-4methyl-6-(2,4,4-trimethylpentyl)-2-pyridone and piroctone olamine.

Sorbitan monocaprylate is harmless dermatologically as well as toxicologically even in very high use, concentrations and supports the antimicrobial action of antimicrobial active ingredients.

It was further found that sorbitan monocaprylate does not decrease the viscosity of a cosmetic, dermatological or pharmaceutical formulation, but even, on the contrary, has slightly thickening properties. Thus, relatively high amounts of sorbitan monocaprylate can be employed without lowering the viscosity of the cosmetic, dermatological or pharmaceutical formulation or favoring a phase separation.

The use concentration of antimicrobial active ingredients needed for an adequate preservation of the cosmetic, dermatological or pharmaceutical formulation can be significantly decreased in combination with sorbitan monocaprylate. By this means, the use of an antimicrobial active ingredient often suffices for the preservation of the cosmetic, dermatological or pharmaceutical formulation.

Sorbitan monocaprylate is liquid at room temperature and, miscible with other antimicrobial active ingredients.

Advantageous to, the liquid and therefore easily manageable compositions according to the invention is, for example, their good formulatability.

Preferably, the one or more antimicrobial active ingredient(s) of component b) is/are selected from the group consisting of the components b1), b3) and b5)

b1) organic acids and their salts selected from benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts, b3) isothiazolinones selected from aqueous compositions containing from 20 to 80% by weight, preferably from 30 to 70% by weight and particularly preferably from 40 to 60% by weight, of methylisothiazolinone, chloromethylisothiazolinone, a mixture of methylisothiazolinone and chloromethylisothiazolinone in the ratio 1:3 and/or benzylisothiazolinone, and b5) pyridones and their salts selected from 1-hydroxy-4-methyl-6-(2,4,4-trimethylpentyl)-2-pyridone and piroctone olamine.

Especially preferably, the one or more antimicrobial active ingredient(s) of component b) is/are selected from the group consisting of the components b1), b3) and b5)

b1) organic acids and their salts selected from benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic-acid, glycolic acid and their salts, b3) aqueous compositions containing from 20 to 80% by weight, preferably from 30 to 70% by weight and particularly preferably from 40 to 60% by weight, of methylisothiazolinone, b5) piroctone olamine.

Among these, in turn, preferably the one or more antimicrobial active ingredient(s) of component b) is/are selected from the group consisting of the components b1) and b5)

b1) organic acids and their salts selected from benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts, b5) piroctone olamine.

In an extremely preferred embodiment of the invention, the one or more antimicrobial active ingredient(s) of component b) is/are selected from the group of organic acids and their salts consisting of benzoic acid, sorbic acid, 3-acetyl-6-methyl-2[H]-pyran-2,4[3H]-dione (dehydroacetic acid), p-methoxybenzoic acid, formic acid, acetic acid, propionic add, lactic acid, undecenoic acid, salicylic acid, glycolic acid and their salts.

Very particularly preferably, the one or more antimicrobial active ingredient(s) of component b) is/are selected from the group of organic acids and their salts consisting of benzoic acid, sorbic acid, 3-acetyl-6-methyl-2[H]-pyran-2,4[3H]-dione (dehydroacetic acid), p-methoxybenzoic acid, propionic acid, lactic acid, salicylic acid, glycolic acid and their salts.

In a further extremely preferred embodiment of the invention, the antimicrobial active ingredient of component b) is piroctone olamine.

In a particularly preferred embodiment of the invention, the liquid compositions according to the invention contain one or more other substances selected from d) water e) antimicrobial active ingredients and f) hydrotropes, in which the antimicrobial active ingredients of component e) and hydrotropes of component f) are different to the antimicrobial active ingredients of component b).

The antimicrobial active ingredients of component e) and the hydrotropes of component f) are different to sorbitan monocaprylate.

In a particularly preferred embodiment of the invention, the liquid compositions according to the invention contain water. In a hereunder in turn preferred embodiment of the invention, the water is contained in the liquid compositions according to the invention in an amount from 0.1 to 35% by weight, preferably from 0.1 to 20% by weight and particularly preferably from 0.5 to 10% by weight.

In a further particularly preferred embodiltnent of the invention, the liquid compositions according to the invention contain one or more other antimicrobial active ingredients, which are different to the antimicrobial active ingredients of component b).

These further antimicrobial active ingredients, which are different to the compounds of component b), are preferably selected from alcohols, as, for example, benzyl alcohol, phenoxyethanol, propylene phenoxyethanol, phenethyl alcohol, 1,2-pentanediol, 1,2-hexanediol, 1,6-hexanediol, 1,2-octanediol, 1,2-decanediol, methylpropanediol and ethylhexylglycerol, glycerol, iodopropyhyl butylcarbamate, 2-bromo-2-nitropropane,1,3-diol, cetyltrimethylammonium chloride, cetylpyridinium chloride, benzethonium chloride, diisobutylethoxyethyl dimethylbenzylammonium chloride, diisobutylphenoxyethoxyethyl dimethylbenzylammonium chloride, N-alkyl-N,N-dimethylbenzylammonium chloride, bromide or saccharinate, trimethylammonium chloride, sodium-aluminum chlorohydroxylactate, triethyl citrate, tricetylmethylammonium chloride, 2,4,4'-trichloro-2'-hydroxydiphenyl ether (triclosan), 3,4,4'-trichlorocarbanilide (triclocarban), diaminoalkylamide, for example L-lysine hexadecylamide, 2-hydroxybiphenyl, chlorbutanulum, 5-amino-1,3-bis(2-ethylhexyl)-5-methylhexahydropyrimidine, 2,4-dichlorobenzyl alcohol, N-(4chlorophenyl-N'-(3,4-dichlorophenyl)urea, 2,4, 4'-trichloro-2'-hydroxydiphenyl ether, poly(hexamethylenediguanide)hydrochloride, 1,2-dibromo-2,4-dicyanobutane, 4,4-dimethyl-1,3-oxazolidine, chloroxylenol, citrate heavy-metal salts, silver chloride, piroctose, pyrithiones and their heavy-metal salts, especially zinc pyrithione, zinc phenolsulfate, famesol, bifonazole, butoconazole, cloconazole, clotrimazole, econazole, enilconazole, fenticonazole, fluconazole, isoconazole, itraconazole, ketoconazole, miconazole, naftifine, oxiconazole, sulconazole, terbinafine, terconazole and tioconazole and combinations of these active substances.

In an especially preferred embodiment of the invention, the liquid compositions according to the invention contain one or more other antimicrobial active ingredients, which are different to the antimicrobial active ingredients of component b), and are selected from alcohols, preferably selected from benzyl alcohol, phenoxyethanol, propylene phenoxyethanol, phenethyl alcohol, 1,2-pentanediol, 1,2-hexanediol, 1,6-hexanediol, 1,2-octanediol, 1,2-decanediol, methylpropanediol, ethylhexylglycerol and glycerol and halogenated preservatives, preferably selected from iodopropynyl butylcarbamate and 2-bromo-2-nitropropane-1,3-diol.

In an extremely preferred embodiment of the invention, the liquid compositions according to the invention contain one or more other antimicrobial active ingredients, which are different to the antimicrobial active ingredients of component b) and are selected from alcohols, preferably selected from the group of alcohols consisting of benzyl alcohol, phenoxyethanol, propylene phenoxyethanol, phenethyl alcohol, 1,2-pentanediol, 1,2-hexanediol, 1,6-hexanediol, 1,2-octanediol, 1,2-decanediol, methylpropanediol, ethylhexylglycerol and glycerol, particularly preferably selected from the group of alcohols consisting of benzyl alcohol, phenoxyethanol, propylene phenoxyethanol, phenethyl alcohol, 1,2-pentanediol, 1,2-hexanediol, 1,6-hexanediol, 1,2-octanediol, 1,2-decanediol, methylpropanediol and ethylhexylglycerol and especially preferably selected from the group of alcohols consisting of benzyl alcohol, phenoxyethanol, 1,2-octanediol and ethylhexylglycerol.

If the liquid compositions according to the invention contain one or more other antimicrobial active ingredients that are different to the antimicrobial active ingredients of component b), these are preferably contained in the liquid compositions according to the invention in an amount from 0.5 to 50% by weight, particularly preferably from 5 to 45% by weight and especially preferably from 10 to 45% by weight.

In the case that the liquid compositions according to the invention contain one or more salts of organic acids, the liquid compositions according to the invention preferably contain from 2 to 35% by weight, particularly preferably from 5 to 20% by weight and especially preferably from 10 to 15% by weight, of water.

In a further particularly preferred embodiment of the invention, the liquid compositions according to the invention contain one or more hydrotropes that are different to the compounds of component b). These hydrotropes are preferably selected from xylene, toluene and cumene sulfonate. Cumene sulfonate is particularly preferred.

If the liquid compositions according to the invention contain one or more hydrotropes that are different to the compounds of component b), the amount of the one or more of these hydrotropes in the liquid compositions according to the invention is preferably in the range from 1 to 15% by weight, particularly preferably from 4 to 10% by weight and especially preferably from 6 to 8% by weight.

In a further particularly preferred embodiment of the invention, the liquid compositions according to the invention contain one or more other additives.

These further additives are preferably selected from antioxidants and solubilizers.

In a further particularly preferred embodiment of the invention, the liquid compositions according to the invention contain one or more antioxidants.

The antioxidants are preferably selected from superoxide dismutase, tocopherol (vitamin E), ascorbic acid (vitamin C), amino acids (e.g. glycine, histidine, tyrosine, tryptophan) and their derivatives, imidazoles (e.g. urocaninic acid) and their derivatives, peptides such as D,L-carnosine, D-carnosine, L-carnosine and their derivatives (e.g. anserine), carotenoids, carotenes (e.g. α-carotene, β-carotene, lycopene) and their derivatives, chlorogenic acid and its derivatives, lipoic acid and its derivatives (e.g. dihydrolipoic acid), aurothioglucose, propylthiouracil and other thiols (e.g. thioredoxin, glutathione, cysteine, cystine, cystamine and their glycosyl, N-acetyl, methyl, ethyl, propyl, amyl, butyl and lauryl, palmitoyl, oleyl, γ-linoleyl, cholesteryl and glyceryl esters) as well as their salts, dilauryl thiodipropionate, distearyl thiodipropionate, thiodipropionic acid and its derivatives (esters, ethers, peptides, lipids, nucleotides, nucleosides and salts) as well as sulfoximine compounds (e.g. buthionine sulfoximine, homocysteine sulfoximine, buthionine sulfone, penta-, hexa-, heptathionine sulfoximine) in very small tolerable doses (e.g. pmol/kg), furthermore (metal) chelators (e.g. α-hydroxy fatty acids, palmitic acid, phytic acid, lactoferrin), α-hydroxy acids (e.g. citric acid, malic acid), humic acid, phytic acid, gallic acid, bile extracts, bilirubin, biliverdin, EDTA, EGTA and their derivatives, unsaturated fatty acids and their derivatives (e.g. γ-linolenic acid, linoleic acid, oleic acid), folic acid and its derivatives, ubiquinone and ubiquinol and their derivatives, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), coniferyl benzoate of benzoin resin, rutic acid and its derivatives, α-glycosylrutin, ferulic acid, furfurylidene glucitol, carnosine, butylhydroxytoluene, butylhydroxyanisole, nordihydroguaiac resin acid, nordihydroguaiaretic acid, trihydroxybutyrophenone, uric acid and its derivatives, mannose and its derivatives, zinc and its derivatives (e.g. ZnO, ZnSO$_4$) selenium and its derivatives (e.g. selenomethionine), stilbenes and their derivatives (e.g. stilbene oxide, trans-stilbene oxide) and superoxide dismutase and suitable derivatives according to the invention (salts, esters, ethers, sugars, nucleotides, nucleosides, peptides and lipids) of these said substances.

Particularly preferred antioxidants are selected from oil-soluble antioxidants.

Especially preferred antioxidants are selected from tocopheryl acetate, BHT (butylhydroxytoluene) and EDTA.

If the liquid compositions according to the invention contain one or more antioxidants, these are preferably contained in the liquid compositions according to the invention in an amount from 0.001 to 30% by weight, particularly preferably from 0.05 to 20% by weight and especially preferably from 0.1 to 5% by weight.

In a further particularly preferred embodiment of the invention, the liquid compositions according to the invention contain one or more solubilizers.

Preferred solubilizers are compounds selected from the group consisting of ethanol, propanol, isopropanol, n-butanol, isobutanol, butylene glycol, 1,2-propylene glycol, polyethylene glycols having a relative molecular mass of 300 to 2000, especially having a relative molecular mass of 300 to 600, triacetin (glycerol triacetate), 1-methoxy-2-propanol and PEG 4-laurate (polyethylene glycol 4-laurate).

Particularly preferred solubilizers are selected from ethanol, butylene glycol and 1,2-propylene glycol and preferably from ethanol and 1,2-propylene glycol. Ethanol is especially preferred.

If the liquid compositions according to the invention contain one or more solubilizers, these are preferably contained in the liquid compositions according to the invention in an amount from 1 to 20% by weight.

In a further particularly preferred embodiment of the invention, the liquid compositions according to the invention contain less than 5% by weight, preferably less than 3% by weight and particularly preferably less than 1% by weight, of water. In an especially preferred embodiment of the invention, the liquid compositions according to the invention contain no water, i.e. they are anhydrous.

The amounts of water indicated in the present application for the liquid compositions according to the invention are always the total amount of water in the liquid compositions according to the invention. In this total amount of water, the amount of water optionally introduced into the liquid compositions according to the invention by means of component b3) is already taken into consideration.

In a further particularly preferred embodiment of the invention, the liquid compositions according to the invention consist of
a) sorbitan monocaprylate and
b) one or more of the antimicrobial active ingredients mentioned under component b).

In a further particularly preferred embodiment of the invention, the liquid compositions according to the invention consist of
a) sorbitan monocaprylate and
b) one or more of the antimicrobial active ingredients mentioned under component b) and
d) water.

In a further particularly preferred embodiment of the invention the liquid compositions according to the invention consist of
a) sorbitan monocaprylate and
b) one or more of the antimicrobial active ingredients mentioned under component b) and
e) one or more other antimicrobial active ingredients that are different to the antimicrobial active ingredients mentioned under component b).

In a further particularly preferred embodiment of the invention, the liquid compositions according to the invention consist of a) sorbitan monocaprylate and
b) one or more of the antimicrobial active ingredients mentioned under component b),
d) water and
e) one or more other antimicrobial active ingredients that are different to the antimicrobial active ingredients mentioned under component b).

Preferably, the liquid compositions according to the invention have a clear appearance.

In a further preferred embodiment of the invention, the liquid compositions according to the invention are free of alcohols R—OH, wherein R is a radical consisting of carbon, hydrogen and optionally oxygen atoms having 5-12, preferably 6-11, carbon atoms, and the carbon atoms can be linked to one another in a linear, branched and/or cyclic manner by means of saturated, unsaturated and/or aromatic carbon-carbon bonds and the radicals can also contain ether units and in which hydrogen atoms and/or hydroxyl groups can be bonded to the individual carbon atoms.

The liquid compositions according to the invention are advantageously suitable for preserving cosmetic, dermatological or pharmaceutical products.

A further subject of the invention is therefore the use of a liquid composition according to the invention for preserving cosmetic, dermatological or pharmaceutical products, preferably creams, cream gels, lotions, shampoos, shower baths, deodorants, antiperspirants, wet wipes, sunscreen formulations or decorative cosmetic articles. In a preferred embodiment of the invention, cosmetic, dermatological or pharmaceutical formulations are preserved.

The liquid compositions according to the invention are furthermore advantageously suitable for the production of cosmetic, dermatological or pharmaceutical products, preferably of cosmetic, dermatological or pharmaceutical formulations.

A further subject of the present invention is therefore the use of a liquid composition according to the invention for the production of cosmetic, dermatological or pharmaceutical products and preferably of cosmetic, dermatological or pharmaceutical formulations.

The term "cosmetic, dermatological or pharmaceutical products" is understood in the context of the present invention as meaning, for example, corresponding formulations.

The cosmetic, dermatological or pharmaceutical products can be, for example, aqueous, aqueous-alcoholic, aqueous-surfactant or alcoholic agents or compositions based on oil, including compositions based on oil in anhydrous form or emulsions, suspensions or dispersions, namely in the form of fluids, foams, sprays, gels, mousse, lotions, creams, powders or wet wipes.

In a preferred embodiment of the invention, the liquid compositions according to the invention are used for preserving wet wipes. In this case, the formulation for preserving applied to the textile fabric can be an emulsion, especially an O/W emulsion, but also a surfactant formulation or an oily composition.

In a further preferred embodiment of the invention, the liquid compositions according to the invention are used for preserving emulsions.

The emulsions can be both water-in-oil emulsions and oil-in-water emulsions, microemulsions, nanoemulsions and multiple emulsions. The production of the emulsions can be carried out in a known manner, i.e. for example by cold, hot, hot/cold or PIT emulsification. Self-foaming, foamy, after-foaming or foamable emulsions and microemulsions are a particularly preferred embodiment of the invention.

A further subject of the present invention is cosmetic, dermatological or pharmaceutical products, preferably cosmetic, dermatological or pharmaceutical formulations, that have been prepared using a liquid composition according to the invention that contains
a) sorbitan monocaprylate and
b) one or more antimicrobial active ingredients selected from the group consisting of the components b1) to b5)
 b1) organic acids and their salts selected from benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts,
 b2) formaldehyde donors selected from DMDM hydantoin, imidazolidinyl urea, diazolidinyl urea and sodium hydroxymethylglycinate,
 b3) isothiazolinones selected from aqueous compositions containing from 20 to 80% by weight, preferably from 30 to 70% by weight and particularly preferably from 40 to 60% by weight, of methylisothiazolinone, chloromethylisothiazolinone, a mixture of methylisothiazolinone and chloromethylisothiazolinone in the ratio 1:3 and/or benzylisothiazolinone,
 b4) paraben esters and their salts selected from methylparaben, sodium methylparaben, ethylparaben, sodium ethylparaben, propylparaben, sodium propylparaben, isobutylparaben, sodium isobutylparaben, butylparaben and sodium butylparaben,
 b5) pyridones and their salts selected from 1-hydroxy-4-methyl-6-(2,4,4-trimethylpentyl)-2-pyridone and piroctone olamine,
or cosmetic, dermatological or pharmaceutical products, preferably cosmetic, dermatological or pharmaceutical formulations, that contain such a liquid composition according to the invention.

A further subject of the present invention is cosmetic, dermatological or pharmaceutical products, preferably cosmetic, dermatological or pharmaceutical formulations, containing
a) sorbitan monocaprylate and
b) one or more antimicrobial active ingredients selected from the group consisting of the components b1) to b5)
 b1) organic acids and their salts selected from benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts,
 b2) formaldehyde donors selected from DMDM hydantoin, imidazolidinyl urea, diazolidinyl urea and sodium hydroxymethylglycinate,
 b3) isothiazolinones selected from aqueous compositions containing from 20 to 80% by weight, preferably from 30 to 70% by weight and particularly preferably from 40 to 60% by weight, of methylisothiazolinone, chloromethylisothiazolinone, a mixture of methylisothiazolinone and chloromethylisothiazolinone in the ratio 1:3 and/or benzylisothiazolinone,
 b4) paraben esters and their salts selected from methylparaben, sodium methylparaben, ethylparaben, sodium ethylparaben, propylparaben, sodium propylparaben, isobutylparaben, sodium isobutylparaben, butylparaben and sodium butylparaben,
 b5) pyridones and their salts selected from 1-hydroxy-4-methyl-6-(2,4,4-trimethylpentyl)-2-pyridone and piroctone olamine.

Preferred among these are cosmetic, dermatological or pharmaceutical products, preferably cosmetic, dermatological or pharmaceutical formulations, containing
a) sorbitan monocaprylate and
b) one or more antimicrobial active ingredients selected from the group consisting of the components b1) and b5)
  b1) organic acids and their salts selected from benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts,
  b5) piroctone olamine.

In a preferred embodiment of the invention, the cosmetic, dermatological or pharmaceutical products according to the invention, preferably the cosmetic, dermatological or pharmaceutical formulations according to the invention, contain
a) sorbitan monocaprylate and
b1) one or more organic acids and/or their salts selected from benzoic acid, sorbic acid, 3-acetyl-6-methyl-2 [H]-pyran-2,4[3H]-dione (dehydroacetic acid), p-methoxybenzoic acid, formic acid, acetic acid, propionic acid, lactic acid, undecenoic acid, salicylic acid, glycolic acid and their salts.

In a further preferred embodiment of the invention, the cosmetic, dermatological or pharmaceutical products according to the invention, preferably the cosmetic, dermatological or pharmaceutical formulations according to the invention, contain
a) sorbitan monocaprylate and
b5) piroctone olamine.

In another preferred embodiment of the invention, the cosmetic, dermatological or pharmaceutical products according to the invention, preferably the cosmetic, dermatological or pharmaceutical formulations, contain
a) sorbitan monocaprylate,
b) one or more antimicrobial active ingredients selected from the group consisting of the components b1) to b5)
  b1) organic acids and their salts selected from benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts,
  b2) formaldehyde donors selected from DMDM hydantoin, imidazolidinyl urea, diazolidinyl urea and sodium hydroxymethylglycinate,
  b3) isothiazolinones selected from aqueous compositions containing from 20 to 60% by weight, preferably from 30 to 70% by weight and particularly preferably from 40 to 60% by weight, of methylisothiazolinone, chloromethylisothiazolinone, a mixture of methylisothiazolinone and chloromethylisothiazolinone in the ratio 1:3 and/or benzylisothiazolinone,
  b4) paraben esters and their salts selected from methylparaben, sodium methylparaben, ethylparaben, sodium ethylparaben, propylparaben, sodium propylparaben, isobutylparaben, sodium isobutylparaben, butylparaben and sodium butylparaben,
  b5) pyridones and their salts selected from 1-hydroxy-4-methyl-6-(2,4,4-trimethylpentyl)-2-pyridone and piroctone olamine, and
e) one or more other antimicrobial active ingredients that are different to the antimicrobial active ingredients mentioned under component b).

Among the cosmetic, dermatological or pharmaceutical products according to the invention mentioned, especially the cosmetic, dermatological or pharmaceutical formulations according to the invention, those are preferred in which the one or the more antimicrobial active ingredients of component e) are selected from
alcohols, preferably selected from benzyl alcohol, phenoxyethanol, propylene phenoxyethanol, phenethyl alcohol, 1,2-pentanediol, 1,2-hexanediol, 1,6-hexanediol, 1,2-octanediol, 1,2-decanediol, methylpropanediol, ethylhexylglycerol and glycerol, and
halogenated preservatives, preferably selected from iodopropynyl butylcarbamate and 2-bromo-2-nitropropane-1,3-diol.

Particularly preferred cosmetic, dermatological or pharmaceutical products according to the invention, especially cosmetic, dermatological or pharmaceutical formulations according to the invention, are those containing
a) sorbitan monocaprylate,
b) one or more antimicrobial active ingredients selected from the group consisting of the components b1) to b5)
  b1) organic acids and their salts selected from benzoic acid, sorbic acid, 3-acetyl-6-methyl-2[H1-pyran-2,4[3H]-dione (dehydroacetic acid), p-methoxybenzoic acid, formic acid, acetic acid, propionic acid, lactic acid, undecenoic acid, salicylic acid, glycolic acid and their salts,
  b2) formaldehyde donors selected from DMDM hydantoin, imidazolidinyl urea, diazolidinyl urea and sodium hydroxymethylglycinate,
  b3) isothiazolinones selected from aqueous compositions containing from 20 to 80% by weight, preferably from 30 to 70% by weight and particularly preferably from 40 to 60% by weight, of methylisothiazolinone, chloromethylisothiazolinone, a mixture of methylisothiazolinone and chloromethylisothiazolinone in the ratio 1:3 and/or benzylisothiazolinone,
  b4) paraben esters and their salts selected from methylparaben, sodium methylparaben, ethylparaben, sodium ethylparaben, propylparaben, sodium propylparaben, isobutylparaben, sodium isobutylparaben, butylparaben and sodium butylparaben,
  b5) pyridones and their salts selected from 1-hydroxy-4-methyl-6-(2,4,4-trimethylpentyl)-2-pyridone and piroctone olamine, and
e) one or more alcohols, preferably selected from benzyl alcohol, phenoxyethanol, propylene phenoxyethanol, phenethyl alcohol, 1,2-pentanediol, 1,2-hexanediol, 1,6-hexanediol, 1,2-octanediol, 1,2-decanediol, methylpropanediol and ethylhexylglycerol.

An especially preferred embodiment of the invention is cosmetic, dermatological or pharmaceutical products according to the invention, especially cosmetic, dermatological or pharmaceutical formulations according to the invention, containing
a) sorbitan monocaprylate,
b) one or more antimicrobial active ingredients selected from the group consisting of the components b1) and b5)
  b1) organic acids and their salts selected from benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts,
  b5) piroctone olamine, and
e) one or more alcohols, preferably selected from benzyl alcohol, phenoxyethanol, propylene phenoxyethanol, phenethyl alcohol, 1,2-pentanediol, 1,2-hexanediol, 1,6-hexanediol, 1,2-octanediol, 1,2-decanediol, methylpropanediol and ethylhexylglycerol.

An extremely preferred embodiment of the invention is cosmetic, dermatological or pharmaceutical products according to the invention, especially cosmetic, dermatological or pharmaceutical formulations according to the invention, containing a) sorbitan monocaprylate,
b1) one or more organic acids and/or their salts selected from benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts, and
e) one or more alcohols, preferably selected from the group of alcohols consisting of benzyl alcohol, phenoxyethanol, propylene phenoxyethanol, phenethyl alcohol, 1,2-pentanediol, 1,2-hexanediol, 1,6-hexanediol, 1,2-octanediol, 1,2-decanediol, methylpropanediol and ethylhexylglycerol.

A further extremely preferred embodiment of the invention is cosmetic, dermatological or pharmaceutical products according to the invention, especially cosmetic, dermatological or pharmaceutical formulations according to the invention, containing a) sorbitan monocaprylate,
b5) piroctone olamine and
e) one or more alcohols, preferably selected from the group of alcohols consisting of benzyl alcohol, phenoxyethanol, propylene phenoxyethanol, phenethyl alcohol, 1,2-pentanediol, 1,2-hexanediol, 1,6-hexanediol, 1,2-octanediol, 1,2,-decanediol, methylpropanediol and ethylhexylglycerol.

The salts of the one or more of the organic acids mentioned under component b1) are preferably in the case of benzoic acid sodium benzoate, potassium benzoate or ammonium benzoate,
in the case of sorbic acid potassium sorbate or ammonium sorbate,
in the case of dehydroacetic acid sodium dehydroacetate, potassium dehydroacetate or ammonium dehydroacetate,
in the case of p-methoxybenzoic acid, sodium p-methoxybenzoate, potassium p-methoxybenzoate or ammonium p-methoxybenzoate,
in the case of formic acid sodium formate, potassium formate or ammonium formate,
in the case of acetic acid, sodium acetate, potassium acetate or ammonium acetate,
in the case of propionic acid sodium propionate, potassium propionate, ammonium propionate or calcium propionate,
in the case of lactic acid sodium lactate, potassium lactate, ammonium lactate or magnesium lactate,
in the case of undecenoic acid sodium undecylenate, potassium undecylenate, ammonium undecylenate, magnesium undecylenate or zinc undecylenate,
in the case of salicylic acid sodium salicylate, potassium salicylate, ammonium salicylate, magnesium salicylate or zinc salicylate, and
in the case of glycolic acid sodium glycolate, potassium glycolate, ammonium glycolate or magnesium glycolate.

In an especially preferred embodiment of the invention, the substances of the components a) and b), based on the finished cosmetic, dermatological or pharmaceutical products according to the invention, preferably the finished cosmetic, dermatological or pharmaceutical formulations according to the invention, are together contained to 0.1 to 4.0% by weight, preferably together to 0.2 to 3.0% by weight, particularly preferably together to 0.3 to 2.5% by weight and especially preferably together to 0.5 to 2.0% by weight in the products or formulations.

In a further especially preferred embodiment of the invention, the substances of the components a), b) and e), based on the finished cosmetic, dermatological or pharmaceutical products according to the invention, preferably the finished cosmetic, dermatological or pharmaceutical formulations according to the invention, are together contained to 0.1 to 4.0% by weight, preferably together to 0.2 to 3.0% by weight, particularly preferably together to 0.3 to 2.5% by weight and especially preferably together to 0.5 to 2.0% by weight in the products or formulations.

In a further preferred embodiment of the invention, the cosmetic, dermatological or pharmaceutical products according to the invention, preferably the cosmetic, dermatological or pharmaceutical formulations according to the invention, are free from alcohols R—OH, wherein R is a radical consisting of carbon, hydrogen and optionally oxygen atoms having 5-12, preferably 6-11, carbon atoms, and the carbon atoms can, be linked to one another in a linear, branched and/or cyclic manner by means of saturated, unsaturated and/or aromatic carbon-carbon bonds and the radicals can also contain ether units and in which hydrogen atoms and/or hydroxyl groups can be bonded to the individual carbon atoms.

In a further preferred embodiment of the invention, the cosmetic, dermatological or pharmaceutical products according to the invention are rinse-off products, especially shampoos, hair rinses, hair lotions, shower baths, shower gels or foam baths.

In a further preferred embodiment of the invention, the cosmetic, dermatological or pharmaceutical products according to the invention are leave-on products, especially day creams, night creams, care creams, nutrient creams, body lotions, ointments or lip care compositions. Further preferred leave-on products are decorative cosmetics, especially make-ups, eyeshadows, lipsticks or mascara.

In a further preferred embodiment of the invention, the cosmetic, dermatological or pharmaceutical products according to the invention are sunscreens. These contain one or more UV filters on an organic or inorganic basis.

In a further preferred embodiment of the invention, the cosmetic, dermatological or pharmaceutical products according to the invention are deodorants and antiperspirants, especially in the form of sprays, sticks, gels or lotions.

In a further preferred embodiment of the invention, the cosmetic, dermatological or pharmaceutical products according to the invention are surfactant-free compositions, especially surfactant-free solid compositions or surfactant-free emulsions.

The cosmetic, dermatological or pharmaceutical products according to the invention, preferably the cosmetic, dermatological or pharmaceutical formulations according to the invention, can contain, as further auxiliaries and additives, surfactants, emulsifiers, cationic polymers, thickeners, film formers, antimicrobial active ingredients, astringents, antioxidants, UV light-screen filters, pigments/micropigments, gelling agents, and further additives customary in cosmetics, as, for example, superfatting agents, moisturizing agents, silicones, stabilizers, conditioning agents, glycerol, preservatives, pearlizing agents, colorants, fragrance and perfume oils, solvents, hydrotropes, opacifiers, fatty alcohols, substances having keratolytic and keratoplastic action, antidandruff agents, biogenic active ingredients (local anesthetics, antibiotics, antiinflammatories, antiallergics, corticosteroids, sebostatics), vitamins, Bisabolol®, Allantoin®, Phytantriol®, Panthenol®, AHA acids (alpha-hydroxy acids), plant extracts, for example Aloe Vera, and proteins.

In a preferred embodiment of the invention, the cosmetic, dermatological or pharmaceutical products are appropriate formulations.

A further subject of the present invention is the use of sorbitan monocaprylate for improving the antimicrobial efficacy of one or more antimicrobial active ingredients selected from the group consisting of the components b1) to b5)
b1) organic acids and their salts selected from benzoic acid, sorbic acid, 3-acetyl-6-methyl-2[H]-pyran-2,4[3H]-dione (dehydrdacetic acid), p-methoxybenzoic acid, formic acid, acetic acid, propionic acid, lactic acid, undecenoic acid, salicylic acid, glycolic acid and their salts,
b2) formaldehyde donors selected from DMDM hydantoin, imidazolidinyl urea, diazolidinyl urea and sodium hydroxymethylglycinate,
b3) isothiazolinones selected from aqueous compositions containing from 20 to 80% by weight, preferably from 30 to 70% by weight and particularly preferably from 40 to 60% by weight, of methylisothiazolinone, chloromethylisothiazolinone, a mixture of methylisothiazolinone and chloromethylisothiazolinone in the ratio 1:3 and/or benzylisothiazolinone,
b4) paraben esters and their salts selected from methylparaben, sodium methylparaben, ethylparaben, sodium ethylparaben, propylparaben, sodium propylparaben, isobutylparaben, sodium isobutylparaben, butylparaben and sodium butylparaben,
b5) pyridones and their salts selected from 1-hydroxy-4-methyl-6-(2,4,4-trimethylpentyl)-2-pyridone and piroctone olamine.

The use of sorbitan monocaprylate is preferred for improving the antimicrobial efficacy of one or more antimicrobial active ingredients selected from the group consisting of the components b1) and b5)
b1) organic acids and their salts selected from benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts,
b5) piroctone olamine.

The use of sorbitan monocaprylate is particularly preferred for improving the antimicrobial efficacy of one or more organic acids and/or their salts selected from the group consisting of benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts.

The use of sorbitan monocaprylate for improving the antimicrobial efficacy of piroctone olamine is furthermore particularly preferred.

In a further preferred embodiment of the invention, among the organic acids and their salts of component b1) benzoic acid and its salts are preferred.

The production of the liquid compositions according to the invention can be carried out, for example, by adding together the individual components, optionally with warming to about 80° C.

The following examples and applications are intended to illustrate the invention more closely, but without restricting it thereto. All percentage details are percentages by weight (% by weight), if not explicitly stated otherwise.

EXAMPLES

I) Liquid Compositions According to the Invention

Examples 1-15

Compositions consisting of
1) 90% sorbitan monocaprylate, 10% benzoic acid
2) 50% sorbitan monocaprylate, 15% dehydroacetic acid, 20% methylparaben, 15% ethanol
3) 40% sorbitan monocaprylate, 20% methylparaben, 20% propylparaben, 20% ethanol
4) 60% sorbitan monocaprylate, 15% potassium sorbate, 20% glyoxalic acid, 5% water
5) 90% sorbitan monocaprylate, 5% piroctone olamine, 5% ethanol
6) 80% sorbitan monocaprylate, 5% piroctone olamine, 1% of 50% strength solution of methylisothiazolinone in water, 14% ethanol
7) 70% sorbitan monocaprylate, 30% DMDM hydantoin
8) 55% sorbitan monocaprylate, 15% methylparaben, 20% DMDM hydantoin, 10% ethanol)
9) 55% sorbitan monocaprylate, 30% lactic acid, 5% piroctone olamine, 10% dehydroacetic acid
10) 50% sorbitan monocaprylate, 15% methylparaben, 15% ethylparaben, 5% piroctone olamine, 1% of 50% strength solution of methylisothiazolinone in water, 14% ethanol
11) 75% sorbitan monocaprylate, 10% sodium hydroxymethylglycinate, 10% propylparaben, 5% propylene glycol
12) 40% sorbitan monocaprylate, 35% 1,2-octanediol, 10% potassium sorbate, 10% phenoxyethanol, 5% water
13) 50% sorbitan monocaprylate, 40% benzyl alcohol, 5% piroctone olamine, 1% of 50% strength solution of methyl isothiazolinone in water, 4% ethanol
14) 50% sorbitan monocaprylate, 30% benzyl alcohol, 15% benzoic acid, 5% piroctone olamine
15) 99% sorbitan monocaprylate, 1% of 50% strength solution of methylisothiazolinone in water The preparation of the compositions of Examples 1 to 15 was carried out by blending the individual components successively with stirring in a finger paddle agitator at stirring speeds of 200-300 revolutions/minute. In part and particularly on addition of organic acids, the composition was warmed to approximately 50-80° C. in order to obtain a homogenous mixture.

II) Investigation of the Efficacy Amplification by Sorbitan Monocaprylate

The following examples show results of challenge tests that were carried out according to the requirements of Ph. Eur. Chapter 5.1.3. The following test organisms are used here as representatives for microorganisms: *Pseudomonas aeruginosa* (gram-negative; abbreviated below as "P. a."), *Staphylococcus aureus* (gram-positive; abbreviated below as "St. a."), *Candida albicans* (yeast fungus; abbreviated below as "C. a.") and *Aspergillus brasiliensis* (mold fungus; abbreviated below as "A. b."). In a challenge test, a cosmetic, dermatological or pharmaceutical formulation is accurately considered as adequately preserved if all four test organisms are passed at least with a B criterion. An A criterion means an outstanding preservation, a B criterion, means an adequate preservation and with an F criterion the test is considered overall as not passed. As a comparison, an unpreserved sample of the respective formulation is additionally tested. The further abbreviations SC=sorbitan monocaprylate, Octopirox®=piroctone olamine apply below.

Example 16

The test system used here is a cream that is difficult to preserve (formulation A).

| Formulation A | |
|---|---|
| Ingredients (INCI) | % by wt. |
| Water | to 100% |
| *Vitis Vinifera* seed oil (Grape seed oil) | 6.0% |
| Caprylic/capric triglyceride | 6.0% |
| Glycerol | 3.0% |
| Cetearyl alcohol | 3.0% |
| Glyceryl stearate | 3.0% |
| *Prunus amygdalus Dulcis* oil (Almond oil) | 2.5% |
| Cetearyl glucoside | 2.0% |
| *Prunus Armeniaca* kernel oil (Apricot kernel oil) | 1.5% |
| *Simmondsia Chinensis* oil (Jojoba oil) | 1.3% |
| Lecithin | 1.0% |
| Guar gum | 0.5% |
| Xanthan gum | 0.5% |
| Sodium citrate | 1.0% |
| Tocopherol acetate | 0.5% |
| Allantoin | 0.3% |
| Panthenol | 0.3% |

Example 16a

In a concentration of 0.4%, benzoic acid does not suffice as an individual antimicrobial active ingredient for the adequate preservation of formulation A. The maximum use concentration of benzoic acid for leave-on products allowed in the EU is 0.5%. By addition of sorbitan monocaprylate, however, the cream can be preserved with constant concentration of the benzoic acid (see Table A).

TABLE A

Preservation of the formulation A with benzoic acid and mixtures of benzoic acid and sorbitan monocaprylate (SC)

| Antimicrobial active ingredients | pH | Test system | Use concentration | P.a. | St.a. | C.a. | A.b. |
|---|---|---|---|---|---|---|---|
| Benzoic acid | 5.5 | cream | 0.4% | A | F | B | B |
| Benzoic acid + SC | " | " | 0.4% + 0.5% | A | F | B | A |
| Benzoic acid + SC | " | " | 0.4% + 1.0% | A | B | B | A |
| Benzoic acid + SC | " | " | 0.4% + 1.5% | A | A | A | A |
| unpreserved | " | " | — | F | F | F | F |

P.a. = *Pseudomonas aeruginosa*
St.a. = *Staphylococcus aureus*
C.a. = *Candida albicans*
A.b. = *Aspergillus brasiliensis*

Example 16b

The same test system (formulation A) cannot be preserved adequately by piroctone olamine (Octopirox®) in a use concentration of 0.05%. By addition of sorbitan monocaprylate, the cream can be protected adequately against the growth of bacteria (see Table B).

TABLE B

Preservation of the formulation A with Octopirox® and mixtures of Octopirox® and sorbitan monocaprylate (SC)

| Antimicrobial active ingredients | pH | Test system | Use concentration | P.a. | St.a. | C.a. | A.b. |
|---|---|---|---|---|---|---|---|
| Octopirox® | 5.5 | cream | 0.05% | F | F | F | F |
| Octopirox® + SC | " | " | 0.05% + 0.5% | A | F | F | F |
| Octopirox® + SC | " | " | 0.05% + 1.0% | A | F | F | F |
| Octopirox® + SC | " | " | 0.05% + 1.5% | A | B | F | F |
| unpreserved | " | " | — | F | F | F | F |

P.a. = *Pseudomonas aeruginosa*
St.a. = *Staphylococcus aureus*
C.a. = *Candida albicans*
A.b. = *Aspergillus brasiliensis*

Example 17

The test system used here is a difficult to preserve shampoo containing milk protein (formulation B).

| Formulation B | |
|---|---|
| Ingredients (INCI) | % by wt. |
| Sodium laureth sulfate | 13.70% |
| Water | to 100% |
| Coco betaine | 6.00% |
| Sodium chloride | 1.40% |
| Hydrolyzed milk protein | 1.00% |

Piroctone olamine (Octopirox®) cannot adequately protect the formulation B against growth of mold fungi in a use concentration of 0.05%. This can be achieved by addition of sorbitan monocaprylate.

Better results are also achieved in this case with the gram-positive bacterium (see Table C).

TABLE C

Preservation of the formulation B with Octopirox® and mixtures of Octopirox® and sorbitan monocaprylate (SC)

| Antimicrobial active ingredients | pH | Test system | Use concentration | P.a. | St.a. | C.a. | A.b. |
|---|---|---|---|---|---|---|---|
| Octopirox® | 5.5 | Shampoo | 0.05% | A | B | A | F |
| Octopirox® + SC | " | " | 0.05% + 0.5% | A | B | A | F |
| Octopirox® + SC | " | " | 0.05% + 1.0% | A | B | A | F |
| Octopirox® + SC | " | " | 0.05% + 1.5% | A | A | A | F |
| Octopirox® + SC | " | " | 0.05% + 2.0% | A | A | A | B |
| unpreserved | " | " | — | F | F | A | F |

P.a. = *Pseudomonas aeruginosa*
St.a. = *Staphylococcus aureus*
C.a. = *Candida albicans*
A.b. = *Aspergillus brasiliensis*

The assignment of the A, B and F criteria is directed by the level of the microorganism count reduction within a fixed time interval, in which only the logarithmic reduction is considered. It was also possible to observe a decrease in the microorganism count in Example 17 with the addition of 0.5% or 1.0% of sorbitan monocaprylate to 0.05% Octopirox® in comparison to the sole use of 0.05% Octopirox®, although this is not reflected in the A, B and F criteria listed in Table C.

III) Cosmetic Formulations Containing Liquid Compositions According to the Invention 15 different formulations were in each case prepared from each of the cosmetic formulations A-M listed below. In fact, each cosmetic formulation A-M was in each case prepared using the individual liquid compositions according to the invention of Examples 1 to 15 ("Blends 1-15").

Example A

Shampoo

| | | | |
|---|---|---|---|
| A | Genapol ® LRO paste | Clariant | 13.70% |
| | Sodium Laureth Sulfate | | |
| | Genagen ® KB | Clariant | 6.00% |
| | Coco Betaine | | |
| | Water | | to 100% |
| B | Sodium chloride | | 1.50% |
| C | Blend 1-15 according to the invention | Clariant | 1.50% |
| D | Citric acid (10% in water) | | 0.08% |

Preparation:
I Mix the components of A
II Add B to I with stirring
III Add C to II
IV Adjust the pH to approximately 7

Example B

Facial Cleanser

| | | | |
|---|---|---|---|
| A | Genapol ® LRO liquid | Clariant | 11.10% |
| | Sodium Laureth Sulfate | | |
| | Perfume | | q.s. |
| B | Water | | to 100% |
| | Genagen ® 3SB | Clariant | 23.30% |
| | Coco Betaine, Sodium Cocoyl Isethionate, Sodium Methyl Cocoyl Taurate | | |
| | Dyestuff solution | | q.s. |
| C | Blend 1-15 according to the invention | Clariant | 1.20% |
| D | Citric acid | | q.s. |

Preparation:
I Mix the components A
II Add the components of B successively to I
III Add C to II with stirring
IV If desired, adjust the pH with C

Example C

Aftershave Gel

| | | | |
|---|---|---|---|
| A | Emulsogen ® HCU | Clariant | 1.50% |
| | Undeceth-8 (and) PEG-40 Hydrogenated Castor Oil | | |
| B | Tocopherol acetate | | 0.20% |
| | Menthol | | 0.20% |
| C | Ethanol | | 30.00% |
| D | Water | | to 100% |
| | Allantoin | Clariant | 0.20% |
| | Allantoin | | |
| | Polyglycol 400 | Clariant | 3.00% |
| | PEG-8 | | |
| | Polyglycol 35000 | Clariant | 1.00% |
| | PEG-800 | | |
| | Blend 1-15 according to the invention | Clariant | 2.00% |
| E | Aristoflex ® AVC | Clariant | 1.00% |
| | Ammonium Acryloyldimethyltaurate/VP Copolymer | | |

Preparation:
I Mix A and B and stir for approximately 5 minutes
II Add C to I and stir until the solution is clear
III Add the components of D successively to II
IV Add E to I and stir until a homogenous formulation is obtained

Example D

Anti-Ageing Face Cream

| | | | |
|---|---|---|---|
| A | Genapol ® T 250 | Clariant | 1.50% |
| | Cetereth-25 | | |
| | Genapol ® DAT | Clariant | 2.00% |
| | PEG-150 polyglyceryl-2 Tristearate and PEG-6 Caprylic/Capric Glyceride | | |
| B | Water | | to 100% |
| C | Aristoflex ® AVC | Clariant | 2.00% |
| | Ammonium Acryloyldimethyltaurate/VP Copolymer | | |
| D | Glycolic acid 30%* | | 6.00% |
| | Blend 1-15 according to the invention | Clariant | 1.80% |

*adjusted to pH 4 with NaOH (content based on free glycolic acid)

Preparation:
I Dissolve A in B with stirring and gentle warming
II Add C to I and stir until the resulting gel is free from lumps
III Add the components of D to and stir until the formulation is homogeneous

Example E

Emulsion for Baby Wet Wipes

| | | | |
|---|---|---|---|
| A | Propylene glycol | | 3.00% |
| | Blend 1-15 according to the invention | Clariant | 2.00% |
| | Emulsogen ® HCO 040 | Clariant | 1.00% |
| | PEG-40 Hydrogenated Castor Oil | | |
| | Perfume | | 0.20% |
| B | Hostaphat ® KL 340 D | Clariant | 1.50% |
| | Trilaureth-4 Phosphate | | |
| | Velsan ® CCT | Clariant | 0.80% |
| | Caprylic/Capric Triglyceride | | |
| C | Water | | to 100% |
| | Tetrasodium EDTA | | 0.10% |
| D | Aristoflex ® BLV | Clariant | 0.20% |
| | Ammonium Acryloyldimethyltaurate/Beheneth-25 Methacrylate Crosspolymer | | |
| E | Citric acid | | q.s. |

Preparation:
I Dissolve the components of A
II Add the components of B successively with stirring to I
III Mix the components of C IV Add D to II
V Add III to IV with stirring
VI Adjust the pH with E to approximately pH 6

Example F

O/W Body Lotion

| | | | |
|---|---|---|---|
| A | Velsan ® CCT<br>Caprylic/Capric Triglyceride | Clariant | 3.50% |
| | Myristyl myristate | | 2.50% |
| | Cetearyl alcohol | | 2.00% |
| | Glyceryl stearate citrate | | 1.00% |
| | Octyldodecanol | | 1.00% |
| B | Aristoflex ® AVC<br>Ammonium Acryloyldimethyltaurate/<br>VP Copolymer | Clariant | 0.60% |
| C | Water | | to 100% |
| | Glycerol | | 7.50% |
| D | Ethanol | | 3.00% |
| | Dimethicone | | 3.00% |
| | Tocopheryl acetate | | 1.00% |
| | *Aloe barbadensis* | | 1.00% |
| | Blend 1-15 according to the invention | Clariant | 2.00% |
| E | Sodium hydroxide | | q.s. |

Preparation:
I Melt the components of A at approximately 70° C.
II Mix the components of C and heat the mixture to approximately 70° C.
III Add B to I when I is completely molten
IV Add II to III
V Add the components of D to IV at 35° C.
VI Adjust the pH with E to approximately pH 6.0-6.5

Example G

Antiperspirant

| | | | |
|---|---|---|---|
| A | Locron ® L<br>Aluminum Chlorohydrate | Clariant | 30.00% |
| | Water | | to 100% |
| | Polyglycol 400<br>PEG-8 | Clariant | 3.00% |
| | Ethanol | | 17.00% |
| | Dyestuff solution | | q.s. |
| | Blend 1-15 according to the invention | Clariant | 1.00% |
| | Fragrance | | 0.30% |
| B | Tylose ® H 4000 G4<br>Hydroxyethylcellulose | | 2.50% |

Preparation:
I Mix the components of A
II Add B to I with constant stirring. Stir further until the viscosity has reached its endpoint and the formulation is homogeneous.

Example H

Cream Rinse

| | | | |
|---|---|---|---|
| A | Genamin ® DSAP<br>Distearyldimonium Chloride | Clariant | 2.50% |
| | Genamin ® CTAC<br>Cetrimonium Chloride | Clariant | 3.00% |
| | Hostacerin ® T-3<br>Ceteareth-3 | Clariant | 1.50% |
| | Cetyl alcohol | | 3.00% |
| B | Water | | to 100% |
| | Blend 1-15 according to the invention | Clariant | 1.00% |
| C | Fragrance | | 0.30% |
| | Dyestuff solution | | q.s. |

Preparation:
I Melt A at approximately 75° C.
II Heat B to approximately 75° C.
III Add II to I with stirring and stir until cooling to 30° C.
IV At approximately 30° C. add C to II with stirring

Example I

Hairstyling Gel

| | | | |
|---|---|---|---|
| A | Sorbitol | | 5.00% |
| | Genamin ® PQ 43<br>Polyquaternium-43 | Clariant | 0.30% |
| B | Water | | to 100% |
| C | Aristoflex ® HMB<br>Ammonium Acryloyldimethyltaurate/<br>Beheneth-25 Methacrylate Crosspolymer | Clariant | 2.00% |
| D | Aminomethyl propanol | | 0.30% |
| | Aristoflex ® A 60<br>VA/Crotonates Copolymer | Clariant | 5.00% |
| | Emulsogen ® HCO 040<br>PEG-40 Hydrogenated Castor Oil | Clariant | 4.00% |
| E | Fragrance | | 0.20% |
| | Blend 1-15 according to the invention | Clariant | 1.00% |
| | Dyestuff solution | | q.s. |
| | Timiron diamond cluster MP-149<br>Mica (and) Titanium Dioxide (for EU: CI 77891) | | q.s. |

Preparation:
I Mix the components of A
II Add B to I
III Swell C in II with stirring
IV Add the components of D one after the other
V Add the components of E one after the other to IV

Example J

Make-Up Remover

| | | | |
|---|---|---|---|
| A | Velsan ® P8-3<br>Isopropyl C12-15 Pareth-9 Carboxylate | Clariant | 5.00% |
| B | Hostapon ® KCG<br>Sodium Cocoyl Glutamate | Clariant | 2.30% |
| | Genagen ® CAB<br>Cocamidopropyl Betaine | Clariant | 3.00% |
| | Genapol ® LA 070<br>Laureth-7 | Clariant | 2.00% |
| | Water | | to 100% |
| | Allantoin<br>Allantoin | Clariant | 0.30% |
| | Aristoflex ® PEA<br>Polypropylene Terephthalate | Clariant | 1.00% |
| | 1,6-Hexanediol | | 2.00% |
| | 1,2-Propanediol | | 2.00% |
| | Polyglycol 400<br>PEG-8 | Clariant | 2.00% |
| | Panthenol | | 0.50% |
| | Lutrol F 127<br>Poloxamer 407 | | 3.00% |
| | Blend 1-15 according to the invention | Clariant | 1.70% |

Preparation:
I Stir the components of B successively into A and stir until a clear solution is obtained

Example K

Lipgloss

| | | | |
|---|---|---|---|
| A | Versagel ® ME 1600<br>Hydrogenated polyisobutene (and) Ethylene/Propylene/Styrene Copolymer (and) Butylene/Ethylene/Styrene Copolymer | | to 100% |
| | SilCare ® silicone 31M50<br>Caprylyl Trimethicone | Clariant | 7.00% |
| | SilCare ® silicone 41M65<br>Stearyl Dimethicone | Clariant | 3.00% |
| | Jojoba oil | | 2.60% |
| | Velsan CCT<br>Capric/Caprylic Triglycerides | Clariant | 1.00% |
| | Isopropyl myristate | | 7.40% |
| B | Gemtone ® Tan Opal<br>Mica and Iron Oxide and TiO$_2$ | | 1.00 to 5.00% |
| | Lake-color | | q.s. |
| C | Blend 1-15 according to the invention | Clariant | 0.50% |
| D | Perfume | | q.s. |

Preparation:
I Heat the components of A to approximately 80-85° C. and stir until a homogenous mixture is obtained. Allow this mixture to cool to 70-75° C.
II Add B and C successively to I with stirring and stir until all constituents are dissolved
III Allow to cool to 45° C. and add D to II, then fill the formulation into the casting molds

Example L

Shimmering Bronze Gel

| | | | |
|---|---|---|---|
| A | Water | | to 100% |
| B | Glycerol | | 5.00% |
| | Polyglycol 35000 S<br>PEG-800 | Clariant | 0.50% |
| | Allantoin<br>Allantoin | Clariant | 0.20% |
| C | Aristoflex ® AVC<br>Ammonium Acryloyldimethyltaurate/VP Copolymer | Clariant | 0.60% |
| | Biron MTU<br>Bismuth Oxychloride | | 3.00% |
| | Flamenco ultra silk<br>Titanium Oxide (and) Mica | | 4.00% |
| | Flamenco sparcle gold<br>Mica (and) Iron Oxide (and) Titanium Oxide | | 7.00% |
| | Cloisonné satin bronze<br>Iron Oxide (and) Mica | | 5.00% |
| | Gemtone Sunstone<br>Mica (and) Iron Oxide (and) Titanium Oxide | | 2.00% |
| | Desert reflections canyon sunset<br>Mica (and) Iron Oxide (and) Titanium Oxide (and) Tin Oxide | | 2.00% |
| | SilCare ® silicone WSI<br>proposed INCI: Glyceryl Carboxy Amodimethicone | Clariant | 1.00% |
| D | Fragrance | | q.s. |
| | Blend 1-15 according to the invention | Clariant | 1.80% |

Preparation:
I Mix the components of B and dissolve them in A with stirring
II Mix the components of C and add them to I with gentle stirring
III Stir at relatively high speed of rotation (approximately 200-250 revolutions/minute) for approximately two hours or until a homogeneous gel is obtained
IV Add D to III with stirring

Example M

Suncream

| | | | |
|---|---|---|---|
| A | SilCare ® silicone WSI<br>proposed INCI: Glyceryl Carboxy Amodimethicone | Clariant | 2.00% |
| | SilCare ® silicone 41M65<br>Stearyl Dimethicone | Clariant | 1.00% |
| | Dow Coring ® 246<br>Cyclopentasiloxane/Cyclohexasiloxane | | 11.00% |
| | Titanium dioxide UV Titan M 262<br>Titanium Dioxide/Dimethicone | | 10.00% |
| | Solaveil CT-100<br>C12-15 Alkyl Benzoate/Titanium Dioxide/Aluminuin Stearate/Polyhydroxystearic Acid/Alumina | | 10.00% |
| | Z-Cote HP1<br>Zinc Oxide | | 8.00% |
| | Butylene glycol | | 3.00% |
| | Hostacerin ® DGI<br>Polyglycenyl-2 Sesquiisostearate | Clariant | 3.00% |
| | Tegosoft ® TN<br>C12-15 Alkyl Benzoate | | 2.00% |
| | Cetiol ® 868<br>Ethylhexylstearate | | 2.00% |
| B | Water | | to 100% |
| | Glycerol | | 5.00% |
| | *Ginko biloba* extract | | 0.70% |
| | Polyglycose | | 0.20% |
| | Disodium EDTA | | 0.20% |
| | Citric acid | | 0.10% |
| | Glycerol | | 5.00% |
| | *Ginko biloba* extract | | 0.70% |
| C | Tocopheryl acetate | | 1.00% |
| | Blend 1-15 according to the invention | Clariant | 1.80% |
| | Sodium chloride | | 1.00% |
| | Aluminum hydroxide | | 0.30% |

Preparation:
I Melt A at approximately 80° C.
II Warm B to approximately 80° C.
III Add II to I at a stirring speed of approximately 300 revolutions/minute. Increase the stirring speed gradually to 500 revolutions/minute and keep up this speed-until the end of the formulation operation. Leave the mixture to cool to 35° C.
IV Add C to III at 35° C. with stirring and leave to cool to room temperature The compositions according to the invention of Examples 1-15 contribute to an increase in biostability in the cosmetic formulations A-M.

The invention claimed is:
1. A liquid composition consisting of
a) from 50 to 99.9% by weight of sorbitan monocaprylate and
b) from 1 to 50% by weight of at least one antimicrobial active ingredient selected from the group consisting of the components b1) to b5)
  b1) organic acids and their salts selected from the group consisting of benzoic acid, sorbic acid, 3-acetyl-6-methyl-2 [H]-pyran-2,4[3H]-dione (dehydroacetic acid), p-methoxybenzoic acid, formic acid, acetic acid, propionic acid, lactic acid, undecenoic acid, salicylic acid, glycolic acid and their salts, b2) formaldehyde donors selected from the group consisting of DMDM hydantoin, imidazolidinyl urea, diazolidinyl urea and sodium hydroxy-methylglycinate, b3) isothiazolinones selected from the group consisting of aqueous compositions containing from 20 to 80% by weight of methylisothiazolinone, chloromethylisothiazolinone, a mixture of methylisothiazolinone and chloromethyl-isothiazolinone in the ratio 1:3 and benzylisothiazolinone, b4) paraben esters and their salts selected from the group consisting of methylparaben, sodium methylparaben, ethylparaben, sodium ethylparaben, propylparaben, sodium propylparaben, isobutylparaben, sodium isobutylparaben, butylparaben and sodium butylparaben, and b5) pyridones and their salts selected from the group consisting of 1-hydroxy-4-methyl-6-(2,4,4-trimethylpentyl)-2-pyridone and piroctone olamine.

2. The liquid composition as claimed in claim 1, wherein the at least one antimicrobial active ingredient of component b) is selected from the group consisting of the components b1), b3) and b5)

b1) organic acids and their salts selected from the group consisting of benzoic acid, sorbic acid, 3-acetyl-6-methyl-2 [H]-pyran-2,4[3H]-dione (dehydroacetic acid), p-methoxybenzoic acid, formic acid, acetic acid, propionic acid, lactic acid, undecenoic acid, salicylic acid, glycolic acid and their salts, b3) isothiazolinones selected from the group consisting of aqueous compositions containing from 20 to 80% by weight of methylisothiazolinone, chloromethylisothiazolinone, a mixture of methylisothiazolinone and chloromethylisothiazolinone in the ratio 1:3 and benzylisothiazolinone, and b5) pyridones and their salts selected from the group consisting of 1-hydroxy-4-methyl-6-(2,4,4-trimethylpentyl)-2-pyridone and piroctone olamine.

3. The liquid composition as claimed in claim 1, wherein the at least one antimicrobial active ingredient of component b) is selected from the group consisting of the components b1), b3) and b5)

b1) organic acids and their salts selected from the group consisting of benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts, b3) an aqueous composition containing from 20 to 80% by weight of methyl isoth iazol inone, and b5) piroctone olamine.

4. The liquid composition as claimed in claim 1, wherein the at least one antimicrobial active ingredient of component b) is selected from the group consisting of the components b1) and b5)

b1) organic acids and their salts selected from the group consisting of benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts, and b5) piroctone olamine.

5. The liquid composition as claimed in claim 1, wherein the at least one antimicrobial active ingredient of component b) is selected from the group consisting of benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts.

6. The liquid composition as claimed in claim 1, wherein the at least one antimicrobial active ingredient of component b) is selected from the group consisting of benzoic acid, sorbic acid, 3-acetyl-6-methyl-2[H]-pyran-2,4[3H]-dione (dehydroacetic acid), p-methoxybenzoic acid, propionic acid, lactic acid, salicylic acid, glycolic acid and their salts.

7. A cosmetic, dermatological or pharmaceutical product, consisting of a) sorbitan monocaprylate and b) at least one antimicrobial active ingredient selected from the group consisting of the components b1) and b5)

b1) organic acid and their salt selected from the group consisting of benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts, and b5) piroctone olamine.

8. The cosmetic, dermatological or pharmaceutical product as claimed in claim 7, consisting of a) sorbitan monocaprylate and b1) at least one organic acid and/or their salt selected from the group consisting of benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts.

9. A process for improving the antimicrobial efficacy of at least one of the antimicrobial active ingredients of component b) as claimed in claim 1 consisting of the step of adding sorbitan caprylate with the antimicrobial active ingredient to the liquid composition.

10. The process as claimed in claim 9 for improving the antimicrobial efficacy of at least one organic acid and/or their salt selected from the group consisting of benzoic acid, sorbic acid, 3-acetyl-6-methyl-2[H]-pyran-2,4[3H]-dione (dehydroacetic acid), p-methoxybenzoic acid, formic acid, acetic acid, propionic acid, lactic acid, undecenoic acid, salicylic acid, glycolic acid and their salts consisting of the step of adding sorbitan caprylate with the at least one organic acid and/or their salt to the liquid composition.

* * * * *

(12) SUPPLEMENTAL EXAMINATION CERTIFICATE

United States Patent
Klug et al.

(10) Number: US 8,969,390 F1
(45) Certificate Issued: May 4, 2016

Control No.: 96/000,140
Primary Examiner: Ling Xu

Filing Date: Mar. 30, 2016

No substantial new question of patentability is raised in the request for supplemental examination. See the Reasons for Substantial New Question of Patentability Determination in the file of this proceeding.

(56) Items of Information

U.S. PATENT DOCUMENTS

| | | |
|---|---|---|
| 9,295,626 | 3/2016 | Pilz et al. |

OTHER DOCUMENTS

Copending U.S. Patent Application No. 14/237,027 (represented by the following file history excerpts: specification filed February 4, 2014; abstract filed February 4, 2014; and claims filed July 16, 2014).

Copending U.S. Patent Application No. 14/237,028 (represented by the following file history excerpts: specification filed February 4, 2014; abstract filed February 4, 2014; and claims filed March 17, 2016).

U.S. Patent Application No. 14/237,032 (represented by the following file history excerpts: specification filed February 4, 2014; abstract filed February 4, 2014; and claims filed February 4, 2014).

Copending U.S. Patent Application No. 14/237,034 (represented by the following file history excerpts: specification filed February 4, 2014; abstract filed February 4, 2014; and claims filed July 10, 2015).

Copending U.S. Patent Application No. 14/237,039 (represented by the following file history excerpts: specification filed February 4, 2014; abstract filed February 4, 2014; and claims filed December 14, 2015).

Copending U.S. Patent Application No. 14/237,042 (represented by the following file history excerpts: specification filed February 4, 2014; abstract filed February 4, 2014; and claims filed December 8, 2015).

Copending U.S. Patent Application No. 14/237,053 (represented by the following file history excerpts: specification filed February 4, 2014; abstract filed February 4, 2014; and claims filed August 7, 2015).

Copending U.S. Patent Application No. 14/237,071 (represented by the following file history excerpts: specification filed February 4, 2014; abstract filed February 4, 2014; and claims filed July 17, 2014).

Copending U.S. Patent Application No. 14/237,076 (represented by the following file history excerpts: specification filed February 4, 2014; abstract filed February 4, 2014; and claims filed July 1, 2015).